United States Patent
Chang

(10) Patent No.: US 7,089,943 B2
(45) Date of Patent: Aug. 15, 2006

(54) LARYNGEAL MASK

(75) Inventor: Eric Chang, Taichung Hsien (TW)

(73) Assignee: Hsiner Co., Ltd., Taichung Hsien (TW)

( * ) Notice: Subject to any disclaimer, the term of this patent is extended or adjusted under 35 U.S.C. 154(b) by 0 days.

(21) Appl. No.: 10/914,093

(22) Filed: Aug. 10, 2004

(65) Prior Publication Data

US 2005/0279361 A1    Dec. 22, 2005

(51) Int. Cl.
*A61M 16/00* (2006.01)

(52) U.S. Cl. .................. 128/207.15; 128/207.14; 128/200.26

(58) Field of Classification Search .......... 128/207.14, 128/207.15, 200.26
See application file for complete search history.

(56) References Cited

U.S. PATENT DOCUMENTS

| | | | | |
|---|---|---|---|---|
| 4,995,388 A * | 2/1991 | Brain | ............... | 128/207.15 |
| 5,771,889 A * | 6/1998 | Pagan | ............... | 128/207.15 |
| 5,896,858 A * | 4/1999 | Brain | ............... | 128/207.15 |
| 5,983,897 A * | 11/1999 | Pagan | ............... | 128/207.15 |
| 6,012,452 A * | 1/2000 | Pagan | ............... | 128/200.26 |
| 6,021,779 A * | 2/2000 | Pagan | ............... | 128/207.15 |
| 6,050,264 A * | 4/2000 | Greenfield | ............... | 128/207.15 |
| 6,116,243 A * | 9/2000 | Pagan | ............... | 128/207.15 |
| 6,439,232 B1 * | 8/2002 | Brain | ............... | 128/207.15 |
| 6,705,322 B1 * | 3/2004 | Chang | ............... | 128/207.15 |
| 6,799,574 B1 * | 10/2004 | Collins | ............... | 128/207.15 |
| 2003/0192548 A1 * | 10/2003 | Chang | ............... | 128/207.14 |

* cited by examiner

*Primary Examiner*—Henry Bennett
*Assistant Examiner*—Andrew Bunin
(74) *Attorney, Agent, or Firm*—Nixon & Vanderhye, P.C.

(57) ABSTRACT

A laryngeal mask includes an inflatable ring which has an outer periphery, an inner periphery with a welded edge projecting inwardly therefrom, and two opposite first and second wall parts extending respectively from the welded edge to the outer periphery. A gas supply tube has an open end which is connected to the inflatable ring along the welded edge, and a peripheral connection part hermetically sealed to the welded edge. A forward guide tab projects forwardly from the peripheral connection part and extends over a portion of the first wall part. Preferably, the forward guide tab is formed integrally with the peripheral connection part and is welded to the portion of the first wall part.

4 Claims, 8 Drawing Sheets

LARYNGEAL MASK

BACKGROUND OF THE INVENTION

1. Field of the Invention

The invention relates to a laryngeal mask, more particularly to an improved laryngeal mask having a forward guide tab projecting forwardly from a welded edge of an inflatable ring.

2. Description of the Related Art

Laryngeal masks are medical aids that are used to administer anesthetic gases to patients. FIGS. 1 and 2 show a conventional laryngeal mask disclosed in U.S. Pat. No. 5,355,879. As shown, the conventional laryngeal mask includes an airway tube 10, an inflatable ring 20 connected to the airway tube 10, and an inflation flexible tube 30 connected to the inflatable ring 20. The airway tube 10 has an inlet end and an opposite end connected to an inner periphery of the inflatable ring 20 in an oblique manner to define an opening 11. A front end wall of the airway tube 10 at the opening 11 has a forward guide part 12 to facilitate insertion of the laryngeal mask into the patient's throat. The inflatable ring 20 is substantially elliptical, and can be inflated and deflated through the flexible tube 30 by operation of a pump (not shown).

In use, the inflatable ring 20 which has not been inflated is inserted into the patient's throat through the patient's mouth, as shown in FIG. 3. By introducing air into the inflatable ring 20 through the flexible tube 30, the inflatable ring 20 can be inflated to seal around the laryngeal inlet so that there is not any clearance between the patient's throat and the inflatable ring 20. It is necessary that the opening 11 be properly aligned with the laryngeal inlet so that anesthetic gases to be administered can be delivered into the trachea without dispersing to the other parts of the body.

However, as the inflatable ring 20 is inserted into the patient's mouth in a deflated state in actual practice, and as the inflatable ring 20 is made of a soft flexible material, insertion of the inflatable ring 20 into the patient's throat is guided only by the forward guide part 12 at the front end wall of the airway tube 10. However, since the forward guide part 12 is at a distance from a forward end of the inflatable ring 20, the guiding effect is not satisfactory, thereby resulting in difficulty when aligning the opening 11 with the patient's laryngeal inlet and in inconvenient installation. Improper installation of the inflatable ring 20 will, in turn, obstruct supply of air into the inflatable ring 20 such that the latter cannot be fully inflated, thereby resulting in clearances between the inflatable ring 20 and the patient's laryngeal inlet. Thus, the anesthetic gases introduced through the airway tube 10 may disperse to other parts of the patient's body.

SUMMARY OF THE INVENTION

Therefore, the object of the present invention is to provide an improved laryngeal mask that can be inflated easily after being inserted into a patient's throat, thereby overcoming the drawback associated with the aforesaid prior art.

Accordingly, a laryngeal mask according to the present invention comprises: an inflatable ring including an outer periphery, an inner periphery defining an opening, a welded edge projecting into said opening from said inner periphery, and two opposite first and second wall parts extending respectively from said welded edge to said outer periphery so as to define an inflatable chamber, said welded edge having a forward edge part and a width which is increased in said forward edge part; a gas supply tube having an open end connected to said inflatable ring along said welded edge, said open end defining an aperture communicated with said opening and having a peripheral connection part hermetically sealed to said welded edge; and a forward guide tab projecting forwardly from said peripheral connection part and said welded edge and extending over a portion of said first wall part, said portion of said first wall part being immediately adjacent to said welded edge and separated from said second wall part.

The laryngeal mask further includes an inflating tube connected fluidly to the inflatable ring. The inflating tube is embedded in a tubular wall of the gas supply tube.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 4:
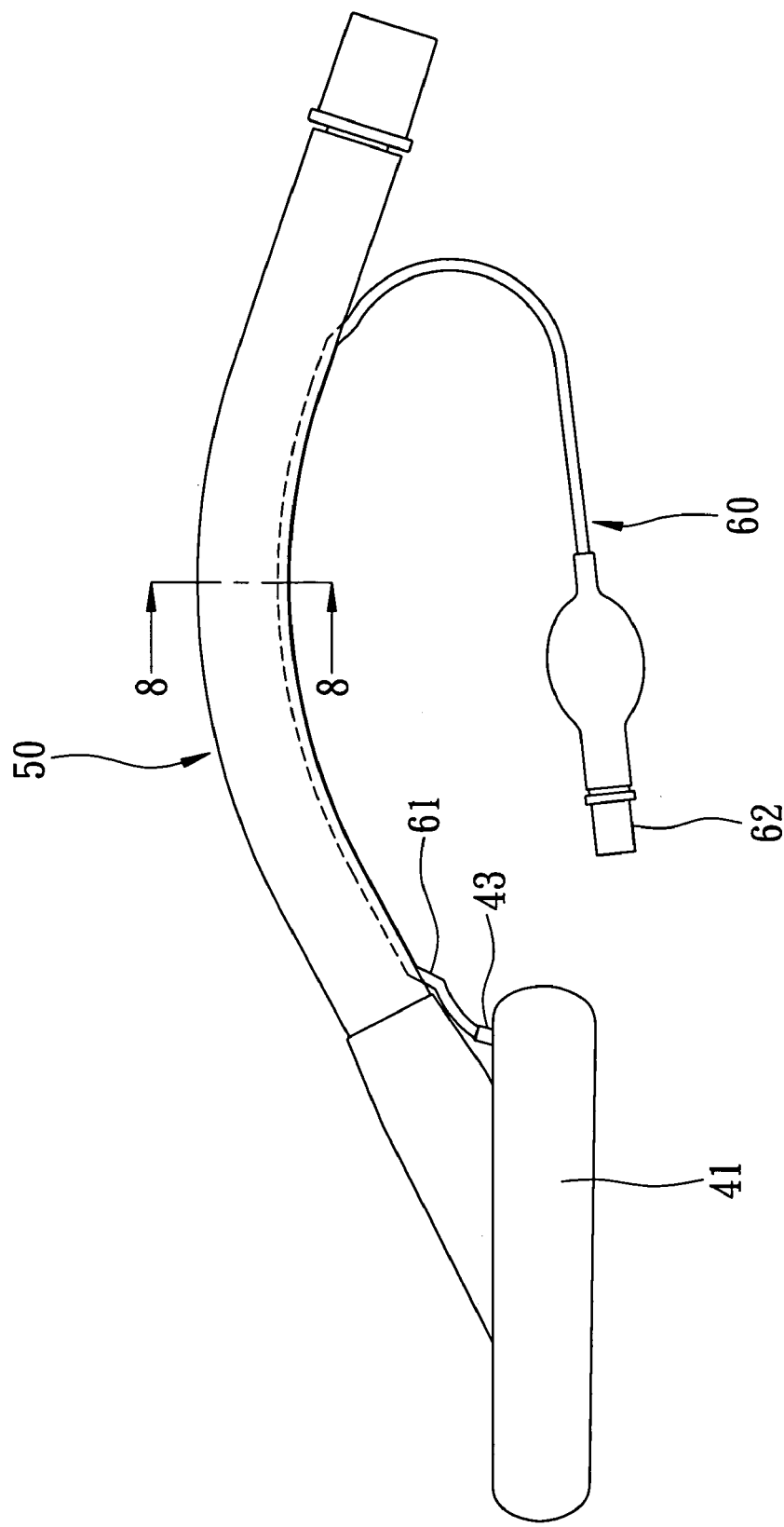
FIG. 4 is a side view of a preferred embodiment of a laryngeal mask according to this invention.
Figure 5:
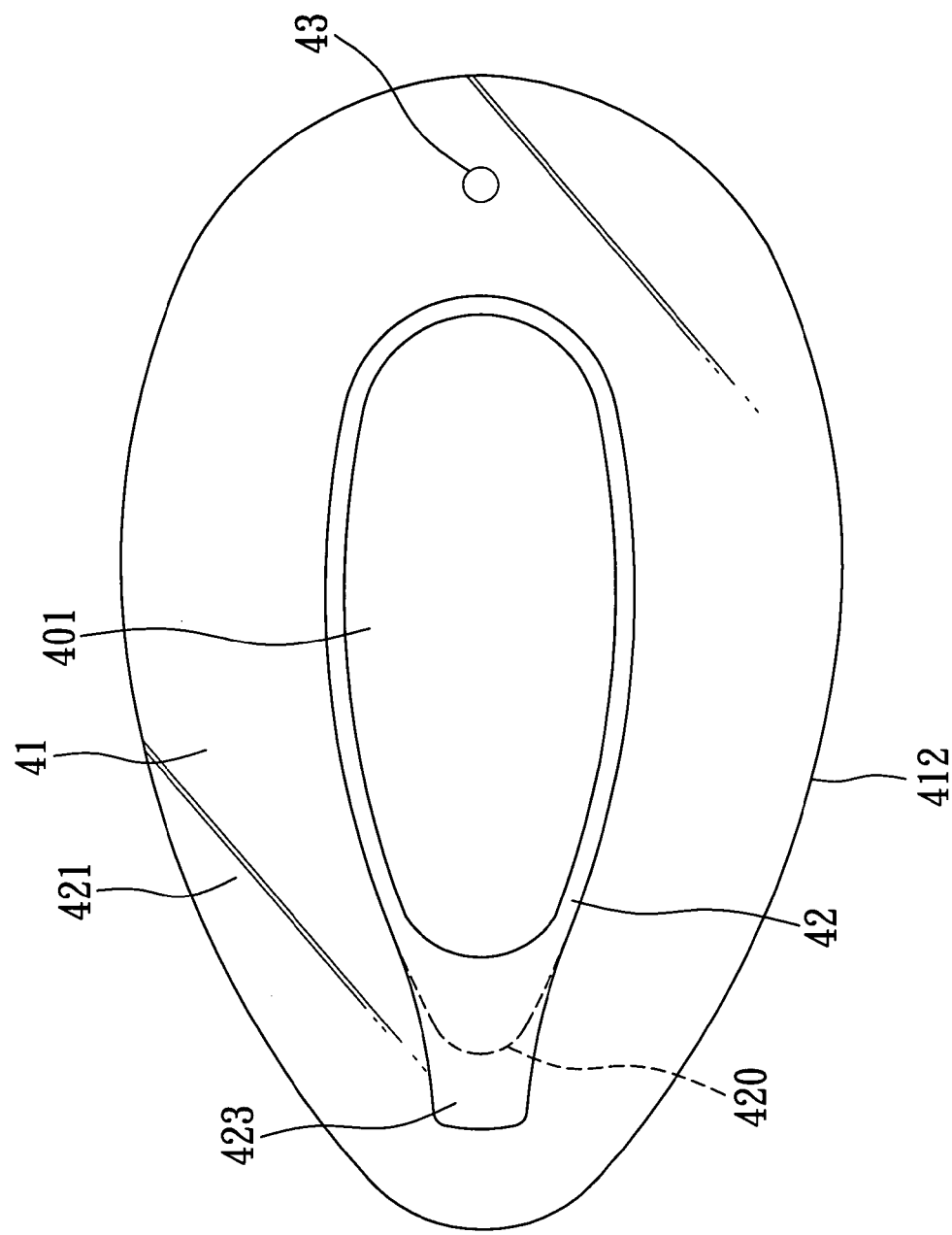
FIG. 5 is a plan view showing an inflatable ring of the preferred embodiment.
Figure 6:
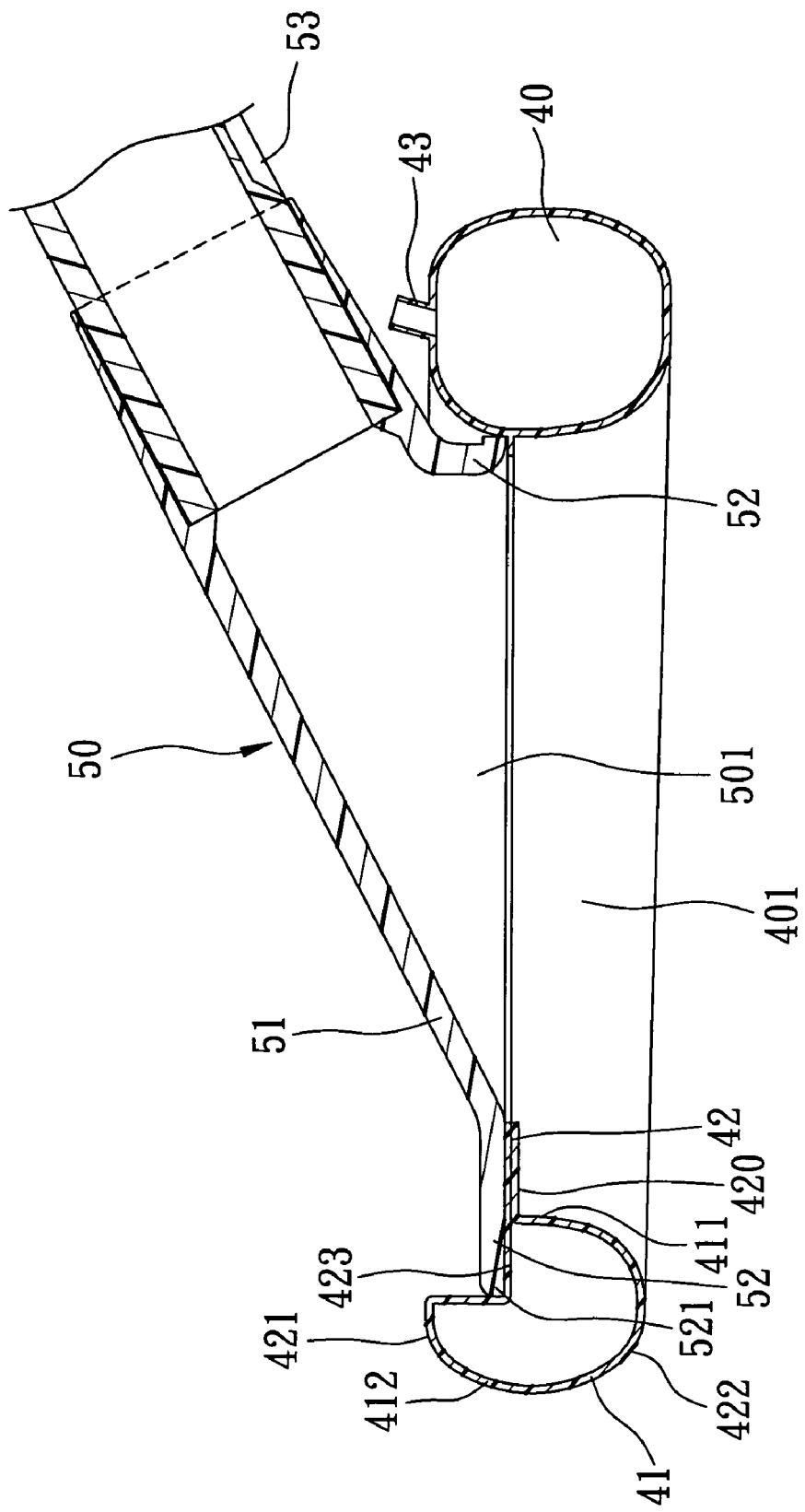
FIG. 6 is a fragmentary sectional view of the preferred embodiment.

Referring to FIGS. 4, 5 and 6, a laryngeal mask embodying the present invention is shown to include an inflatable ring 41, a gas supply tube 50 attached to the inflatable ring 41 and an inflating unit 60 for inflating the inflatable ring 41.

The inflatable ring 41 has an inner periphery 411 defining an opening 401, an outer periphery 412, two opposite first and second wall parts 421 and 422 each extending from the inner periphery 411 to the outer periphery 412 to define an inflatable chamber 40. The first and second wall parts 421 and 422 are welded to each other at the inner periphery 411 so that a welded edge 42 projects inwardly from the inner periphery 411. The welded edge 42 extends along the inner periphery 411 and has a forward edge part 420. The width of the welded edge 42 is increased in the forward edge part 420 compared to the width of the remaining part of the welded edge 42. The first wall part 421 of the inflatable ring 41 has a portion 423 which extends forwardly beyond the forward edge part 420 of the welded edge 42 and which is immediately adjacent to the welded edge 42. Numeral 43 denotes an adaptor disposed on the inflatable ring 41.

The gas supply tube 50 has an open end 51 which defines an aperture 501 in communication with the opening 401 of the inflatable ring 41. The open end 51 has a peripheral connection part 52 superimposed on and welded to the welded edge 42 of the inflatable ring 41. A forward guide tab 521 projects forwardly from the welded edge 42 and the peripheral connection part 52 to extend over the portion 423 of the first wall part 421 of the inflatable ring 41. Preferably, the forward guide tab 521 is formed integrally with the peripheral connection part 52 of the gas supply tube 50 and is welded to the portion 423 of the first wall part 421 of the inflatable ring 41 so that the peripheral connection part 521 is hermetically sealed to the welded edge 42. The portion 423 of the first wall part 421 is separated from the second wall part 422 so that a gas confining space is formed as a part of the inflatable chamber 40 between the first and second wall parts 421, 422 and beneath the forward guide tab 521.

Figure 8:
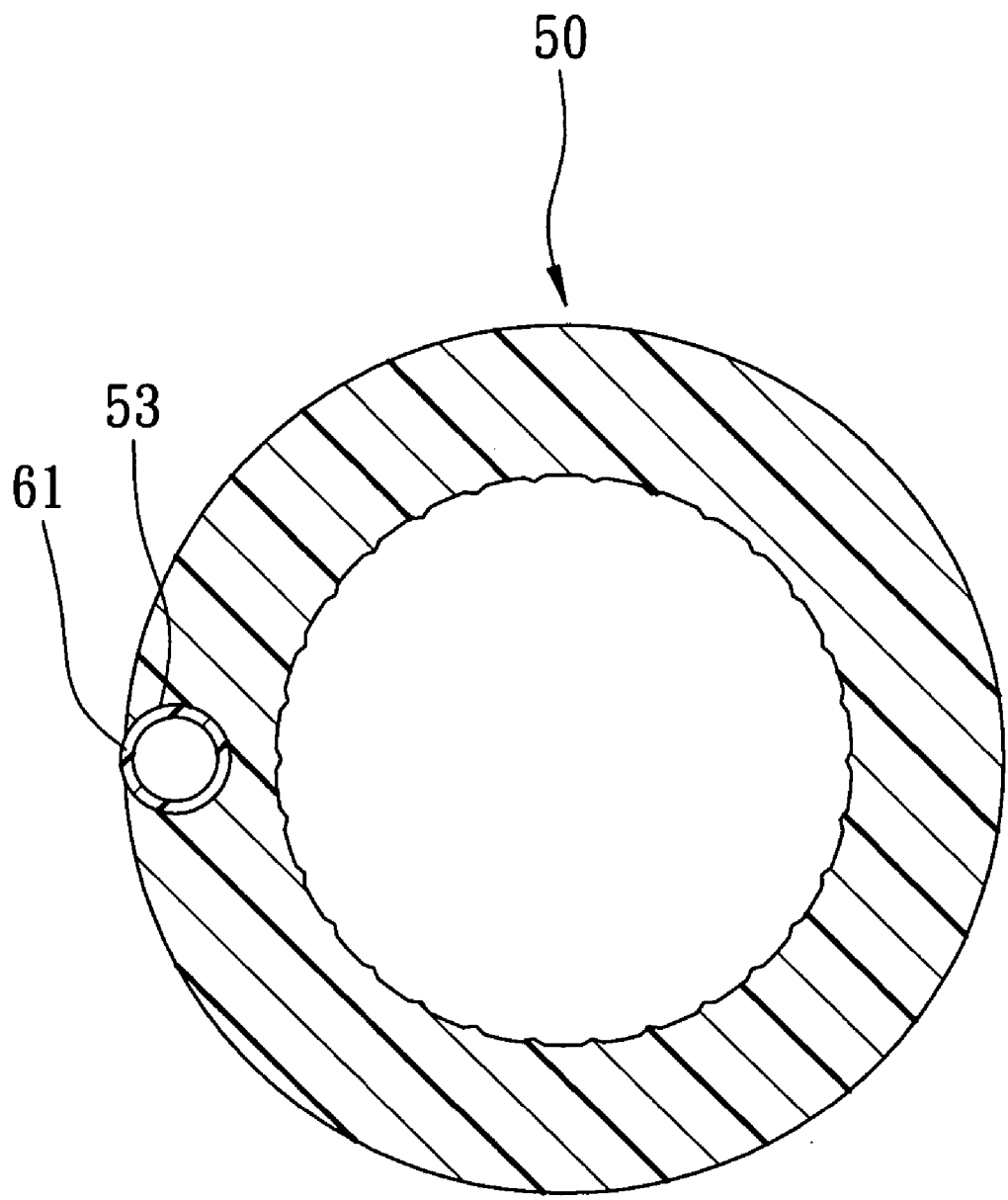
FIG. 8 is a sectional view taken along line 8—8 of FIG. 4.

The inflating unit 60 includes an inflating tube 61 connected to the adaptor 43 of the inflatable ring 41 and an inflating valve 62. As shown in FIG. 8, the inflating tube 61 is received in a groove 53 formed in a tubular wall of the gas supply tube 50 so that the inflating tube 61 is embedded within the tubular wall of the gas supply tube 50 and extends along the length of the gas supply tube 50.

Figure 3:
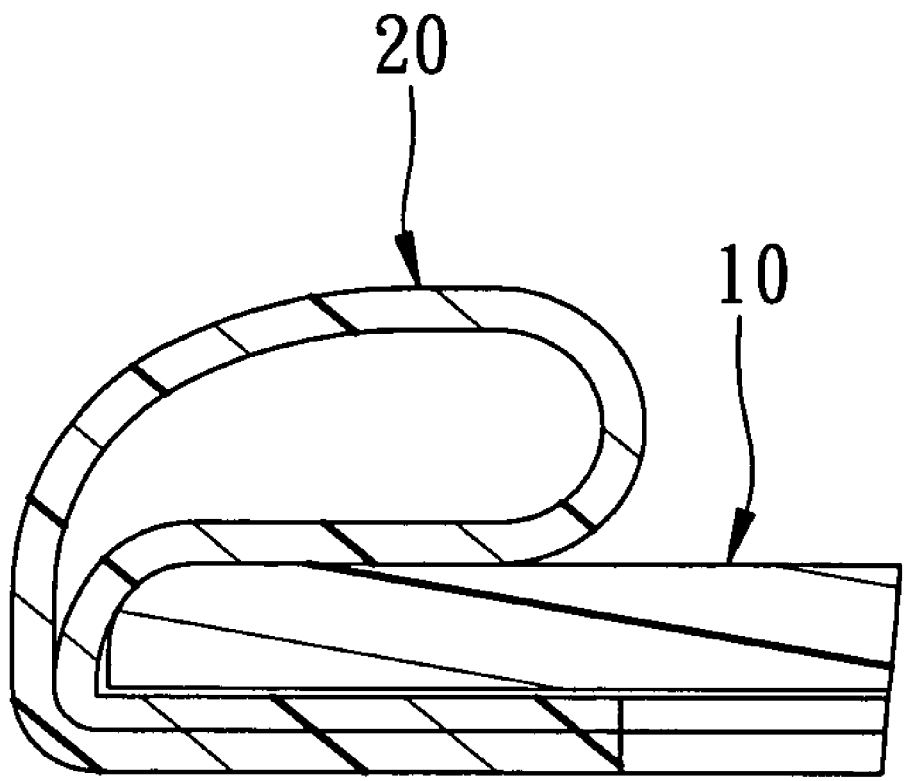
FIG. 3 is a fragmentary sectional view of the laryngeal mask of FIG. 1.
Figure 7:
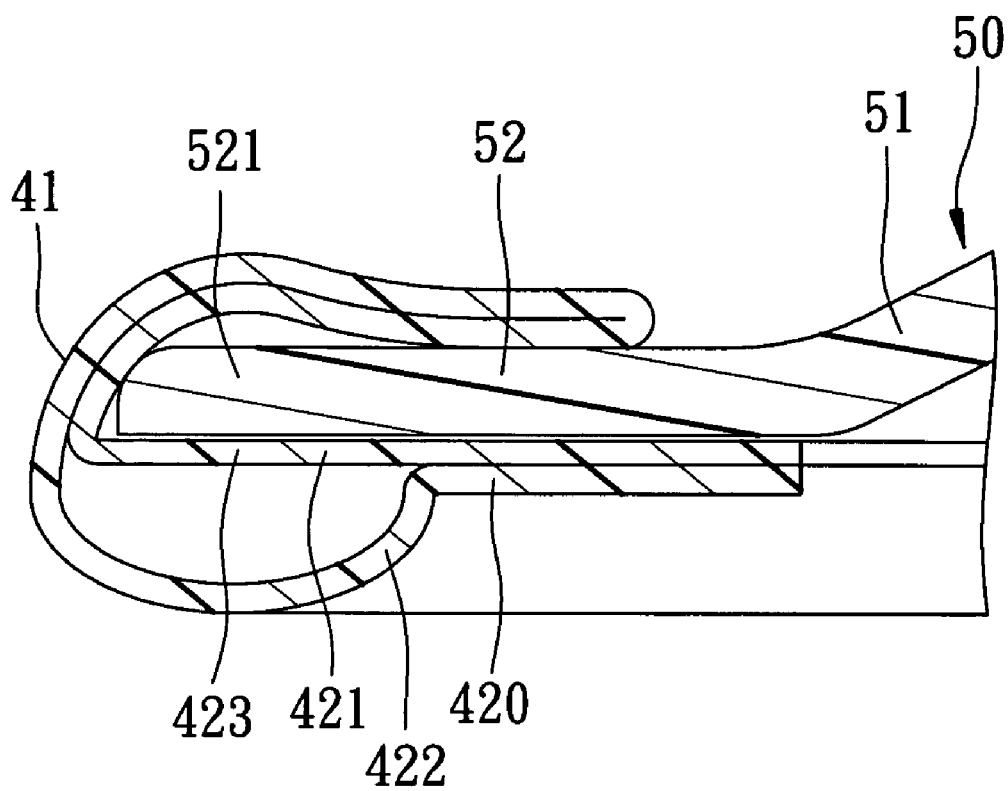
FIG. 7 is another fragmentary sectional view of the preferred embodiment with the inflatable ring being uninflated.

When the laryngeal mask of this embodiment is inserted into the patient's throat, the forward guide tab 521 which has a measure of rigidity and resiliency, provides guidance toward the patient's throat. As shown in FIG. 7, when the laryngeal mask of the present invention is inserted into the patient's throat, the first and second wall parts 521, 422 of the inflatable ring 41 will be folded close to the front edge of the forward guide tab 521. However, since the portion 423 of the first wall part 421 which is welded to the forward guide tab 521 is separated from the second wall part 422, residual air in the inflatable ring 41 will be received in the space confined by the first and second wall parts 421, 422 beneath of the forward guide tab 521. As such, when the inflatable ring 41 is inflated, the inflating air can be forced through the folded part of the inflatable ring 41 formed at the front of the forward guide tab 51, thereby facilitating the unfolding of the folded part and inflation of the inflatable ring 41. On the contrary, in the prior art, residual air is received in a space of the inflatable ring 20 above the forward guide part 12 of the inflatable ring 20, as shown in FIG. 3, when the inflatable ring 20 is inserted into the patient's throat because there is no space for receiving residual air beneath the forward guide part 12. Due to the absence of such a residual air receiving space beneath the forward guide part 12, there is a risk that the folded part of the inflatable ring 20 cannot be unfolded and inflated because of difficulties in forcing air through the folded part of the inflatable ring 20.

Figure 1:
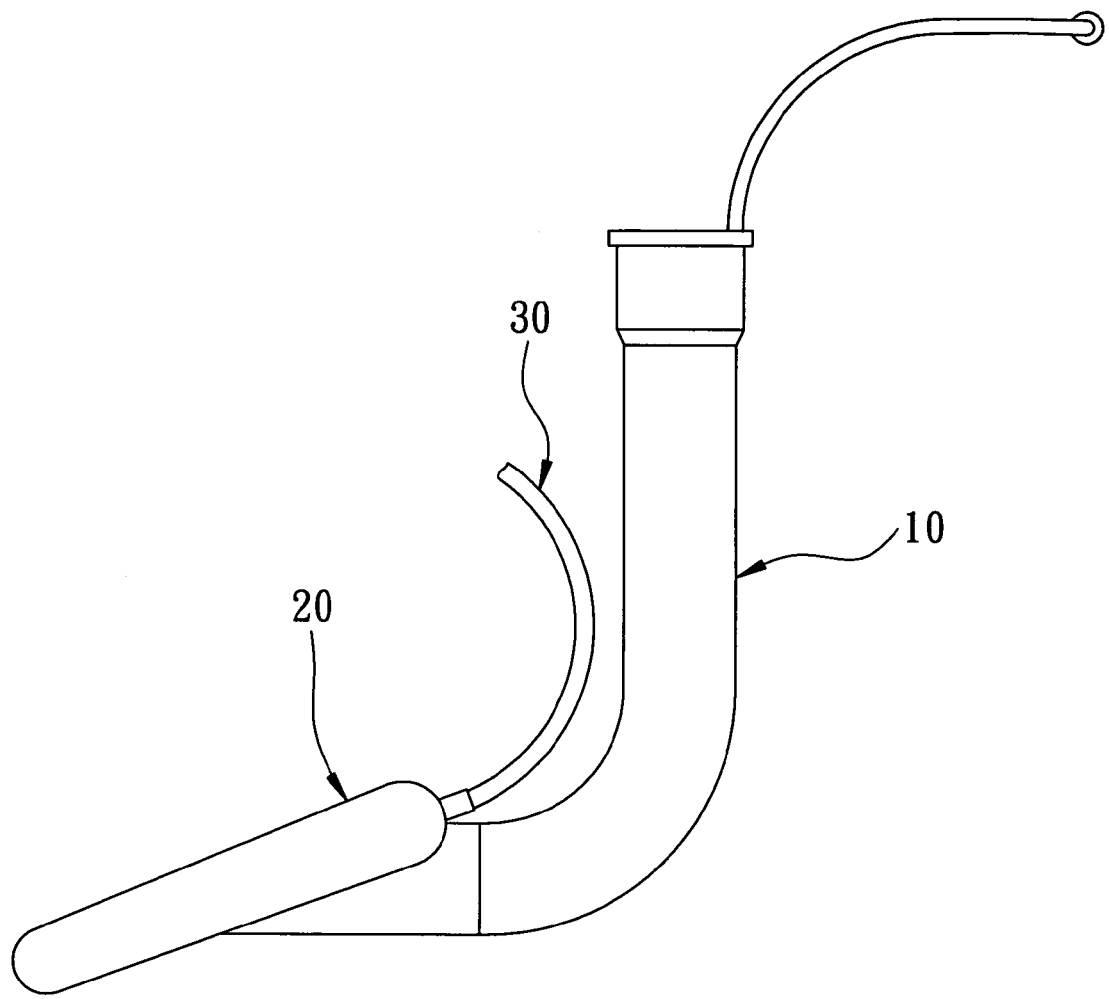
FIG. 1 is a schematic view of a laryngeal mask disclosed in U.S. Pat. No. 5,355,879.
Figure 2:
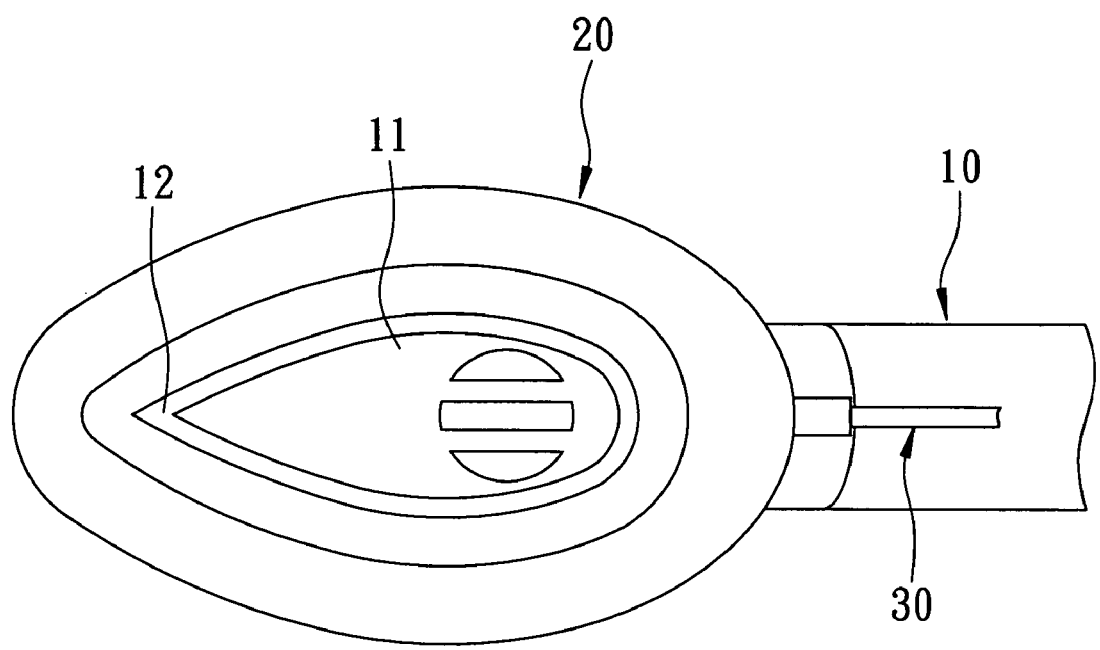
FIG. 2 is a fragmentary plan view of the laryngeal mask of FIG. 1.

Furthermore, compared to the laryngeal mask shown in FIGS. 1–3, the gas supply tube 50 according to the present invention may be manufactured by making a slight change in the configuration of a mold used to fabricate the conventional airway tube 10, and the inflatable ring 41 of the present invention may be made by slightly modifying the configuration of a mold used to fabricate the conventional inflatable ring 20. Therefore, the production of the laryngeal mask according to the present invention will not substantially increase the manufacturing costs.

Moreover, as the inflating tube 61 is embedded in the tubular wall of the gas supply tube 50, the inflating tube 61 will not be exposed to the throat of the patient when the laryngeal mask of the present invention is used, thus eliminating possible discomfort which may be caused to the patient.

While the present invention has been described in connection with what is considered the most practical and preferred embodiment, it is understood that this invention is not limited to the disclosed embodiment but is intended to cover various arrangement included within the spirit and scope of the broadest interpretation so as to encompass all such modifications and equivalent arrangements.

I claim:

1. A laryngeal mask comprising:
    an inflatable ring including an outer periphery, an inner periphery defining an opening, a welded edge projecting into said opening from said inner periphery, and two opposite inflatable first and second wall parts extending from said welded edge to said outer periphery so as to define an inflatable chamber, said welded edge having a forward edge part and a width which is increased in said forward edge part;
    a gas supply tube having an open end connected to said inflatable ring along said welded edge, said open end defining an aperture communicated with said opening and having a peripheral connection part welded to said welded edge; and
    a forward guide tab projecting forwardly from said peripheral connection part and said forward edge part of said welded edge and extending over an outer surface of a portion of said first wall part, said portion of said first wall part being immediately adjacent to said welded edge and separated from said second wall part, said forward guide tab being welded to said portion of said first wall part, said portion of said first wall part being substantially coplanar with said peripheral connection part and said forward edge part of said welded edge, said inflatable ring being indented at said portion to hide said forward guide tab when said inflatable ring is inflated.

2. The laryngeal mask as claimed in claim 1, wherein said forward guide tab is integrally formed with said peripheral connection part of said air supply tube.

3. The laryngeal mask as claimed in claim 2, further comprising an inflating tube connected to said inflatable ring.

4. The laryngeal mask as claimed in claim 3, wherein said gas supply tube has a tubular wall, said inflating tube being embedded in said tubular wall and extending along the length of said tubular wall.

* * * * *